United States Patent [19]

Chow et al.

[11] Patent Number: 4,997,422
[45] Date of Patent: Mar. 5, 1991

[54] HYPODERMIC SYRINGE WITH NEEDLE SHIELD

[76] Inventors: Peter P. Chow; Josephine N. Lo; Loren A. Chow, all of 2317 Byrnes Road, Minnetonka, Minn. 55343

[21] Appl. No.: 304,324

[22] Filed: Jan. 31, 1989

[51] Int. Cl.$^5$ ............................................. A61M 5/32
[52] U.S. Cl. ................................... 604/198; 604/263
[58] Field of Search .............. 604/198, 195, 192, 187, 604/263, 112

[56] References Cited

U.S. PATENT DOCUMENTS

| | | |
|---|---|---|
| 2,571,653 | 10/1951 | Bastien . |
| 2,925,083 | 2/1960 | Craig . |
| 3,306,290 | 2/1967 | Weltman . |
| 3,527,216 | 9/1970 | Snyder . |
| 3,563,239 | 2/1971 | Hill ...................................... 604/112 |
| 3,584,626 | 6/1971 | Johansson . |
| 4,026,287 | 5/1977 | Haller . |
| 4,425,120 | 1/1984 | Sampson et al. . |
| 4,631,057 | 12/1986 | Mitchell . |
| 4,650,468 | 3/1987 | Jennings, Jr. . |
| 4,664,653 | 5/1987 | Sagstetter et al. . |
| 4,702,739 | 10/1987 | Milorad . |

*Primary Examiner*—John D. Yasko
*Attorney, Agent, or Firm*—James R. Haller; Gregory P. Kaihoi; Mary P. Bauman

[57] ABSTRACT

A needle shielding device attachable to a hypodermic syringe for protecting a user from contacting the tip of a needle. The device comprises a generally cylindrical needle shield slidably engaging a syringe body for protecting a user from being stuck by the needle tip of the syringe. The needle shield continuously frictionally engages and grips the syringe body as the shield is moved between a retracted position wherein the needle extends forwardly of the needle shield and a extended position wherein the needle tip is protectively enclosed by the needle shield.

9 Claims, 2 Drawing Sheets

HYPODERMIC SYRINGE WITH NEEDLE SHIELD

FIELD OF THE INVENTION

The invention relates to a needle shield for use with a syringe to protect a user from contacting the tip of the syringe needle.

BACKGROUND OF THE INVENTION

Syringe needles are commonly used in the medical field for extracting blood samples or injecting medication into a patient. The needles are commonly carried at the end of a hypodermic syringe barrel, a blood drawing tube, or other similar apparatus, and may include conventional removable needle covers which, once removed, are discarded. It is particularly desirable to shield the user from coming into physical contact with a used needle which may be contaminated with blood or tissue fluid which may contain infectious substances. There is a growing concern about accidental exposure to the AIDS virus, for example. The greatest hazard has been shown to be the capping or uncapping the needle with the use of the currently used needle cap. It would be desirable to provide a syringe needle with an inexpensive, simple device that would protect the user from being stuck by a contaminated needle. Various attempts have been made to shield used needles, and a representative shielding structure is shown in U.S. Pat. Nos. 4,425,120, 4,631,057 and 4,702,739. For the most part, such structures have been expensive and cumbersome and have not gained acceptance by the medical community.

SUMMARY OF THE INVENTION

The invention provides a needle shield for use with hypodermic syringes and the like for protecting a user from contacting the tip of the syringe needle. The needle shield of the invention is selectively slidable between an extended position wherein the tip of the needle is protectively enclosed by the needle sheath and a retracted position wherein the needle extends forwardly of the protective sheath so that it can perform its normal functions of withdrawal or injection. The needle shield of the invention frictionally engages the external periphery of a hypodermic syringe to allow for controlled movement between a retracted and an extended position. In a preferred embodiment, the needle shield is formed as a longitudinally split, hollow cylinder which has inner contact positions that frictionally grip the outer surface of the associated syringe barrel.

DETAILED DESCRIPTION OF THE PREFERRED EMBODIMENT

Figure 1:
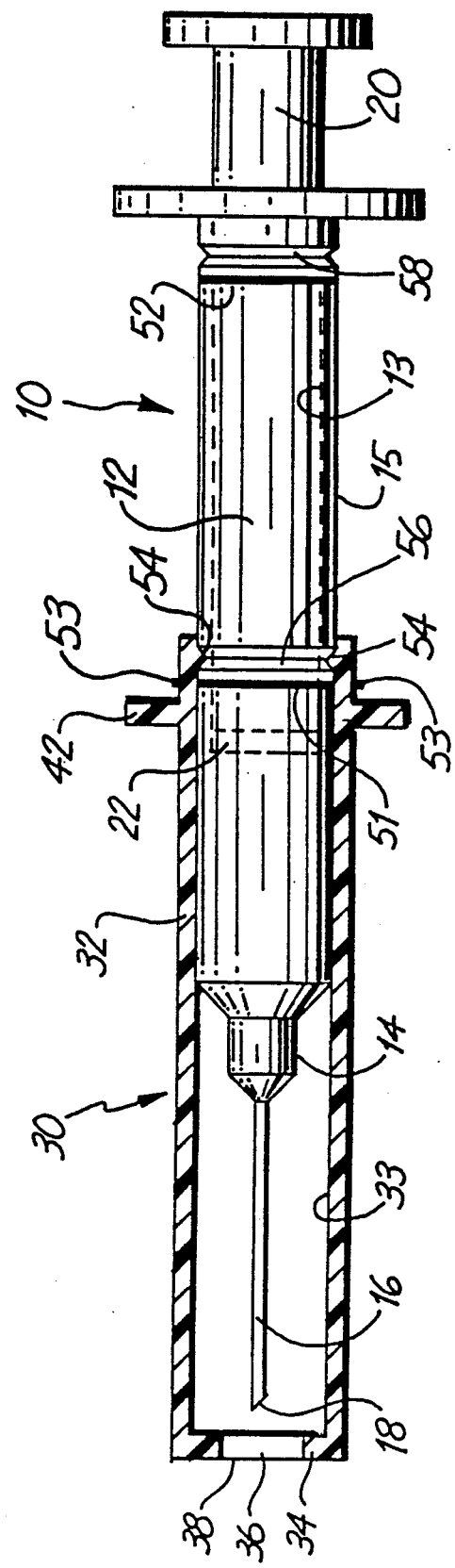
FIG. 1 is a perspective view in partial cross section of a hypodermic syringe utilizing the device of the invention.

FIG. 1 illustrates a hypodermic syringe 10 having a generally cylindrical barrel 12, the barrel having a forward end 14 upon which is carried a forwardly projecting needle 16 having a tip 18. The syringe barrel 12 has a longitudinal bore 13 within which is closely carried a portion of a plunger 20 having a stopper 22 forming a liquid-tight seal across the bore opening. The plunger 20 is axially slidable within the bore 13 to move fluid inwardly and outwardly of the needle tip 18.

Figure 2:
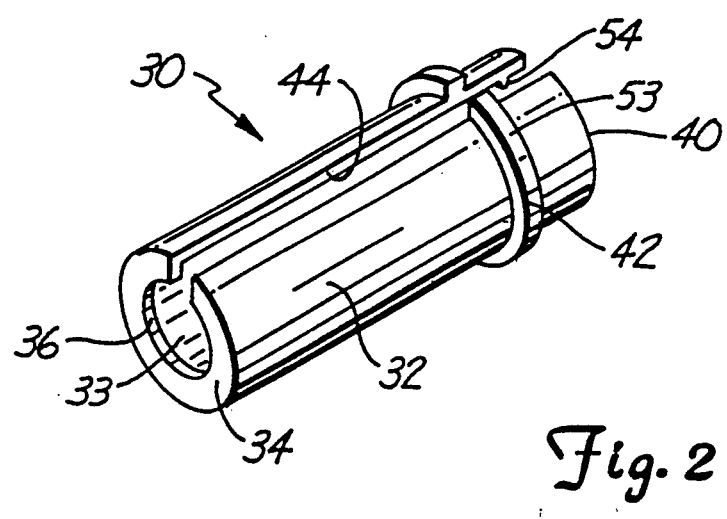
FIG. 2 is a perspective view of the needle sheath of the invention.

The syringe barrel 12 preferably has a smooth outer surface 15 upon which may be carried a needle shield 30. The needle shield 30 typified in FIGS. 1 and 2 comprises a generally cylindrical barrel 32 defining an interior bore 33 having contact positions for closely contacting the outer surface of the syringe barrel 12. At its forward end, the needle shield 30 includes an inwardly directed flange 34 defining a forward opening 36 having a diameter smaller than the diameter of the bore 33. The forward opening 36 may be covered by a penetrable membrane 38, as shown in FIG. 1, preferably comprised of a rubber material or the like, through which the needle 16 may pass to draw a blood sample from a patient or perform other functions. The needle shield 30 includes a rearward opening 40, as illustrated in FIG. 2, for reception of the syringe barrel 12. An external grip such as the outwardly extending, finger grippable flange 42 is provided to facilitate sliding the needle shield 30 axially with respect to the syringe barrel 12.

In a preferred embodiment, the needle shield 30 is split longitudinally to form a longitudinally extending slot 44 which enables the needle shield 30 to be elastically radially expanded to receive and frictionally engage the syringe barrel 12 to hold the needle shield 30 in a desired position with respect to the syringe barrel 12.

Syringes are commercially packaged with or without the needle attached. If the needle is already attached (often with a slender, removable sheath protecting the needle), the syringe 10 may be inserted needle end first into the rearward opening 40 of the needle shield 30. The needle shield 30 may be elastically radially expanded by manually enlarging the width of the slot 44 so that the needle shield 30 receives the barrel 12, the shield having contact portions which contact outer surface portions of the syringe barrel 12. The resilient forces of the material comprising the needle shield 30 will cause the needle shield 30 to grippingly but slidably engage the syringe barrel 12. The needle shield 30 is preferably formed of a suitable clear plastic, although other materials may be used as desired.

When the needle shield 30 is placed upon the syringe barrel 12, it may be moved axially with respect to the syringe barrel 12 from a retracted position into an extended position. The extended position is shown in FIG. 1 wherein the needle tip 18 is safely enclosed within the bore 33 of the needle shield 30, thus preventing a user from contacting the needle tip 18. The device may be packaged, stored or transported in the extended position to prevent a user from contacting the needle tip 18.

If the syringe is packaged without a needle already attached, then the needle shield 30 (without membrane 38) should first be slid over the syringe barrel 12 to a retracted position. The syringe preferably is packaged, stored and transported with the needle shield 30 already attached. Before use, a needle 16 is attached to the forward end of the syringe barrel at 14. After the syringe is used, the needle shield is moved to the extended position to protectively enclose the needle.

In order to expose the needle tip 18 for use in drawing a blood sample, the needle shield 30 in its extended position may be gripped by the fingers about the finger-engaging flange 42 and moved rearwardly with respect to the syringe barrel 12 until the needle 16 protrudes forwardly of the forward opening 36 sufficiently to draw a blood sample from a patient or inject a fluid. The frictional contact between the needle shield 30 and the syringe barrel 12 serve to prevent undesired relative movement between these two parts. The constant frictional contact enables a user to easily control the sliding of the needle shield 30 with respect to the syringe barrel 12 which is desirable for safe needle use.

Position marking means, such as line markings 51 and 52, as shown in FIG. 1, may be carried by the syringe barrel 12 to indicate, when properly aligned with a line marking 53 carried by the needle shield 30, the extended and retracted positions of the device, respectively. The line markings may simply comprise narrow colored rings extending around the periphery of the device. Any suitable position marking means may be employed in the needle shield of the invention.

A pair of annular grooves 56, 58 ma be recessed into the outer surface of the syringe barrel 12 as shown in FIG. 1 for reception of a radially inwardly directed protrusion 54 carried by the needle shield 30. The grooves facilitate retention of the needle shield 30 in the extended and retracted positions, respectively. Preferably, the grooves 56, 58 extend entirely around the periphery of the syringe body 12 and are generally "V" shaped in longitudinal cross section. A protrusion 54, preferably "V" shaped in cross-section to closely engage the grooves 56, 58, partially or entirely around the needle shield 30 adjacent its rearward opening 40. In use, the needle shield 30 is slidable between the extended and retracted positions, the protrusion 54 engaging the grooves 56, 58 to positively define the extended and retracted positions, respectively. The protrusion 54 is configured so as not to hinder the sliding motion of the shield axially along the syringe body between its extended and retracted positions. Other suitable retention means as are known in the art may be employed in the device to releasably retain the needle shield in the extended and retracted positions.

The membrane 38 may be formed of rubber sheeting or the like, and may be carried across the forward opening 36 of the needle shield 30 to prevent the needle 16 from becoming contaminated by or from contaminating the surrounding environment.

The needle shield 30 of the invention may be formed of a resilient plastic such as polyethylene, and is sized to closely fit syringe bodies having different diameter sizes. The needle shield is generally formed having a slightly smaller diameter bore 33 than the respective syringe body 12 upon which the needle shield is placed so that the shield may resiliantly or elastically expand when placed over a syringe barrel. The size of these respective components ensures a close frictional fit between them the needle shield 30 being expandable due to its longitudinally directed slot 44.

While preferred embodiment of the present invention has been described, it should be understood that various changes, adaptations and modifications may be made therein without departing from the spirit of the invention and the scope of the appended claims.

What is claimed is:

1. A hypodermic syringe having a syringe barrel and a needle protruding forwardly from the barrel, and a shield for shielding the needle to protect a user from coming into contact therewith, the shield comprising a generally cylindrical barrel having an interior bore and forward and rearward ends, the forward end of the barrel defining an opening for passage forwardly therethrough of a needle and the rearward end of the barrel defining an opening for reception of the syringe barrel, the shield barrel being carried about and movable longitudinally of the syringe barrel between a retracted rearward position in which the needle protrudes forwardly beyond the end of the shield barrel and an extended forward position in which the shield barrel shieldingly surrounds the needle, the cylindrical shield barrel including a longitudinal slot extending the length of the barrel to enable the shield to radially expand to receive and to closely and frictionally engage the periphery of the syringe barrel, the interior bore of the shield having contact positions for closely contacting the outer surface of the syringe barrel so as to frictionally and slidably engage the syringe barrel continuously as the shield is moved between its extended and retracted positions.

2. A hypodermic syringe having a syringe barrel and a needle protruding forwardly from the barrel, and a shield for shielding the needle to protect a user from coming into contact therewith, the shield comprising a generally cylindrical barrel having forward and rearward ends, the forward end of the barrel defining an opening for passage forwardly therethrough of a needle and the rearward end of the barrel defining an opening for reception of the syringe barrel, the shield barrel being carried about and movable longitudinally of the syringe barrel between a retracted rearward position in which the needle protrudes forwardly beyond the end of the shield barrel and an extended forward position in which the shield barrel shieldingly surrounds the needle, the cylindrical shield barrel including a longitudinal slot extending the length of the barrel and enabling the shield to radially expand to receive the syringe barrel and to closely and frictionally engage the periphery of the syringe barrel continuously as the shield is moved between its extended and retracted positions.

3. The hypodermic syringe of claim 2 wherein the forward end of the shield barrel includes a radially inwardly directed flange having a needle-receiving opening therethrough which is smaller than the opening at the rearward end of the barrel.

4. The hypodermic syringe of claim 2 including gripping means carried by the shield and adapted to be readily gripped by the fingers of a user to remove the shield longitudinally of the syringe barrel.

5. The hypodermic syringe of claim 2 including cooperating means carried by the syringe barrel and shield for releasably restraining the shield, when in its forward extended position, from moving rearwardly upon the syringe barrel toward its rearward retracted position.

6. A hypodermic syringe having a syringe barrel and a needle protruding forwardly from the barrel, and a shield for shielding the needle to protect a user from coming into contact therewith, the shield comprising a generally cylindrical barrel having forward and rearward ends, the forward end of the barrel defining an opening for passage forwardly therethrough of a needle and the rearward end of the barrel defining an opening for reception of the syringe barrel, the shield barrel being carried about and movable longitudinally of the syringe barrel between a retracted rearward position in which the needle protrudes forwardly beyond the end of the shield barrel and an extended forward position in which the shield barrel shieldingly surrounds the needle, the shield including means frictionally and slidingly engaging the syringe barrel continuously as the shield is moved between its extended and retracted positions, position marking means carried by the syringe barrel and shield for marking the extended and retracted positions, the position marking means comprising an annular colored ring carried by the shield at a position near its rearward end, and at least a pair of annular colored rings axially spaced and carried by the syringe barrel, the ring carried by the shield being alignable with the rings carried by the barrel to define extended and retracted positions.

7. The hypodermic syringe of claim 2, wherein said shield barrel is formed of a substantially clear plastic material.

8. The hypodermic syringe of claim 2, wherein said shield barrel is formed of polyethylene.

9. The hypodermic syringe of claim 2, further comprising a penetrable membrane substantially covering said forward opening of said shield barrel.

* * * * *